United States Patent [19]

Vogler

[11] Patent Number: 5,533,518
[45] Date of Patent: Jul. 9, 1996

[54] BLOOD COLLECTION ASSEMBLY INCLUDING MECHANICAL PHASE SEPARATING INSERT

[75] Inventor: Erwin A. Vogler, Newhill, N.C.

[73] Assignee: Becton, Dickinson and Company, Franklin Lakes, N.J.

[21] Appl. No.: 231,548

[22] Filed: Apr. 22, 1994

[51] Int. Cl.[6] .................................................. A61J 1/00
[52] U.S. Cl. .................................... 128/760; 604/403
[58] Field of Search ..................... 604/403, 408, 604/411, 415, 416; 128/760, 763, 764

[56] References Cited

U.S. PATENT DOCUMENTS

| 3,395,696 | 8/1968 | Brown et al. | 128/764 |
| 4,050,451 | 9/1977 | Columbus . | |
| 4,113,097 | 9/1978 | Finn | 604/415 X |
| 4,125,186 | 11/1978 | Meierhoefer | 604/416 X |
| 4,234,083 | 11/1980 | Cohen | 604/416 X |
| 4,308,232 | 12/1981 | Crouther et al. | 604/403 X |
| 4,420,517 | 12/1983 | Ali | 604/403 X |
| 4,492,634 | 1/1985 | Villa-Real | 604/403 X |
| 4,856,533 | 8/1989 | Anraku et al. | 604/403 X |
| 5,086,784 | 2/1992 | Levine et al. | 128/760 X |
| 5,186,972 | 2/1993 | Williams et al. . | |
| 5,248,531 | 9/1993 | Nagai et al. | 604/403 X |
| 5,261,903 | 11/1993 | Dhaliwal et al. | 604/415 X |

FOREIGN PATENT DOCUMENTS

| 685978 | 1/1953 | United Kingdom | 604/415 |
| 92/16144 | 10/1992 | WIPO | 128/760 |

*Primary Examiner*—Sam Rimell
*Attorney, Agent, or Firm*—Richard E. Brown

[57] ABSTRACT

A blood collection assembly includes a tube, which may be evacuated, and an insert therein. The insert is descendably affixed to the tube wall and, after separating a blood sample taken in the tube into solid and liquid phases, descends during centrifugation and comes to rest at the solid-liquid interface on a projection from the tube bottom. An interior surface of the assembly may be modified to render it clot activating. The invention includes a method for preparing a blood sample for analysis using the assembly.

10 Claims, 3 Drawing Sheets

BLOOD COLLECTION ASSEMBLY INCLUDING MECHANICAL PHASE SEPARATING INSERT

BACKGROUND OF THE INVENTION

1. Field of the Invention

This invention relates to blood collection and, more particularly, relates to a blood sample collection and separation assembly and method for its use.

2. Background

Blood samples are routinely taken in evacuated tubes. One end of a double-ended needle is inserted into a patient's vein. The other end of the needle then punctures a stopper covering the open end of the tube so that the vacuum in the tube draws the blood sample through the needle into the tube. Using this technique, a plurality of samples can be taken using a single needle puncture of the skin.

Prior to clinical examination, blood collected in evacuated tubes often must be separated into a liquid fraction of plasma or serum and a solid fraction of packed or clotted cells. It is conventional in the art to perform this separation by centrifugation. A problem which often arises is remixing of the solid and liquid phases, after centrifugation, when the tube is handled, particularly when physical separation of the two phases is attempted.

Thus, it is also conventional in the art to provide some means to maintain the separation of the solid and liquid phases after the centrifugation is complete. Practically all modern blood collection and serum separation devices use a thixotropic gel as the phase separator. These devices rely on the specific gravity of the gel to position the gel at the solid-liquid interface. The gel is initially placed in the bottom of the tube so that the gel moves upwardly to reach the interface. Use of a thixotropic gel as phase separator is disclosed in U.S. Pat. No. 4,050,451 to Colombus.

Problems with thrixotropic gels are related to narrow formulation specifications required to maintain correct thixotropic behavior and specific gravity which greatly complicate high-volume manufacturing. Slow changes in the gel formulation with aging causes product performance problems and limits shelf life. Also, constituents of the gel in the form of gel particles can significantly contaminate serum or plasma and affect downstream chemistry analysis or chemistry analyzing instruments. The present invention is directed to overcoming these disadvantages.

SUMMARY OF THE INVENTION

A blood collection assembly includes a container, preferably a tube of glass or plastic, having a bottom wall continuous with a side wall. The side wall defines an open end and the bottom wall defines a closed end. Together, the bottom and side walls define an inside wall surface. The open end may be covered by a puncturable stopper and the tube may be evacuated.

The assembly includes a mechanical insert for separating blood phases within the interior volume of the tube. The insert is descendably immobilized against the upper inside wall surface of the tube and has a passageway which is coaxially aligned with a projection arising from the bottom of the tube. The tube may contain an additive useful in blood separation or analysis, such as an anticoagulant or clotting agent, or the assembly may include a surface which has been treated to promote clotting.

Another aspect of the invention is a method for taking a blood sample using the assembly of the invention. A blood sample is delivered to the bottom of the tube by puncture of the stopper. The tube is centrifuged to separate the sample into a liquid phase of serum or plasma and a solid phase of packed cells or clot. The insert is then caused to descend through the liquid phase, which passes upwardly through the passageway, and seat securely on the projection at the interface between the liquid and solid layers.

Thus, the invention provides a blood collection assembly having a mechanical, non-gel separator for liquid and solid blood phases. The separator becomes locked securely between the phases and does not move if the tube is moved or jarred. Clean separation of the phases independent of technician skill level is achieved.

DETAILED DESCRIPTION

While this invention is satisfied by embodiments in many different forms, there will herein be described in detail preferred embodiments of the invention with the understanding that the present disclosure is to be considered as exemplary of the principles of the invention and is not intended to limit the invention to the embodiments illustrated and described. The scope of the invention will be measured by the appended claims and their equivalents.

The blood collection assembly of the invention may include any container having a closed end and an open end. Suitable containers are, for example bottles, vials, flasks and the like, preferably tubes. The invention will hence-forth be described in terms of the preferred tube.

Figure 1:
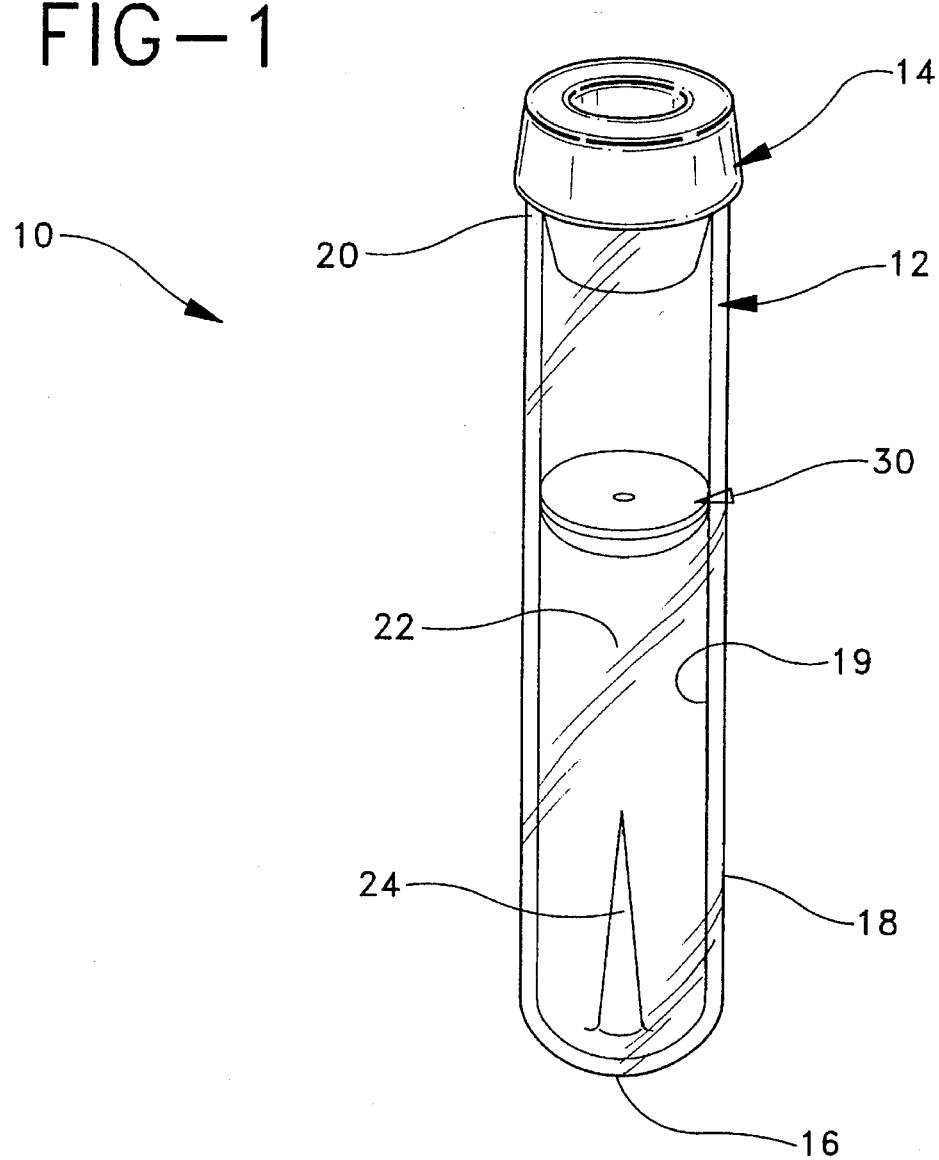
FIG. 1 is a perspective view of a blood collection assembly of the invention.

Adverting now to the drawings, FIGS. 1–4 illustrate a preferred embodiment of a blood collection assembly 10 of the invention. In FIG. 1, assembly 10 includes a tube 12 and a puncturable stopper 14. Tube 12 has a bottom wall 16 and a side wall 18 defining an open end 20 into which stopper 14 may be placed. Side wall 18 has an inside wall surface 19. Bottom wall 16, side wall 18 and stopper 14 enclose an interior volume 22 of the tube which preferably is evacuated. The assembly includes a tapered spike 24 which rises vertically from and is anchored to bottom wall 16. The preferred spike is solid and integral with the tube body and formed during molding of the tube.

Figure 2:
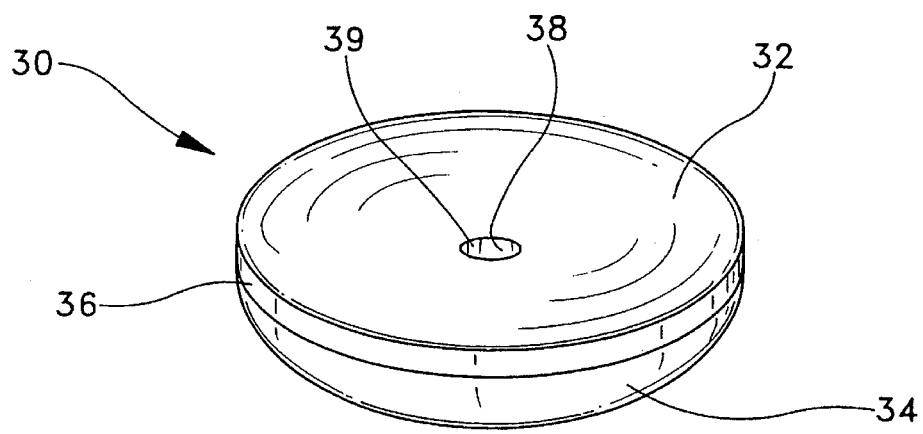
FIGS. 2–4 illustrate embodiments of the phase-separating insert of the invention.

The assembly of the invention includes an insert 30 descendably immobilized in interior volume 22. FIG. 2 illustrates the preferred insert 30 in the form of an annular dish. Dish 30 has a concave top wall 32, a convex bottom wall 34, and a substantially vertical side wall 36. A passageway 38 having a side wall 39 passes through the dish from top wall 32 to bottom wall 34 and is positioned coaxially with and engages tapered spike 24 of the tube when insert 30 descends during centrifugation, as described below.

Figure 3:
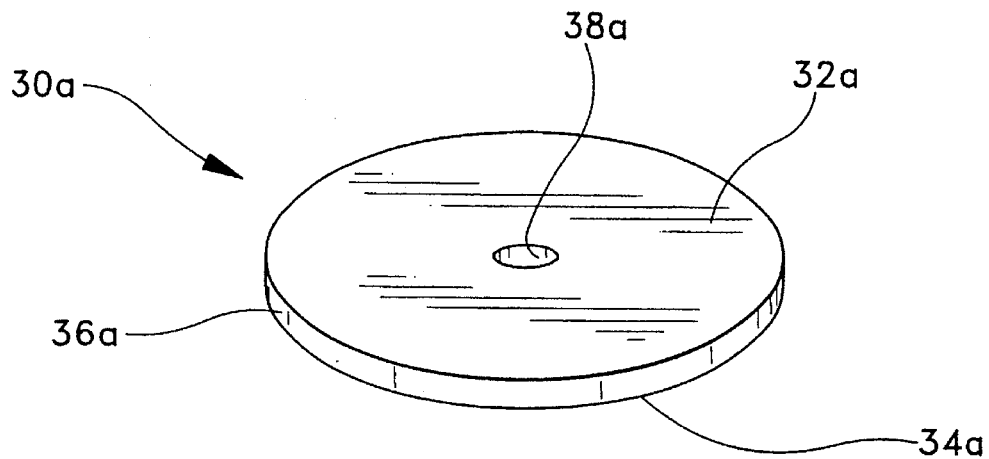

The degree of concavity of top wall 32 is not critical. Thus, while FIG. 2 is an illustration of the preferred insert having the shape of a shallow dish, it is not intended to limit the insert to this shape. FIG. 3 shows the insert in the shape of a disc 30a having a substantially flat top wall 32a, bottom wall 34a, side wall 36a and passageway 38a. (In FIGS. 2 to 6, elements which are the same or substantially the same as elements previously described are given the same reference number followed by a letter suffix.)

Figure 4:
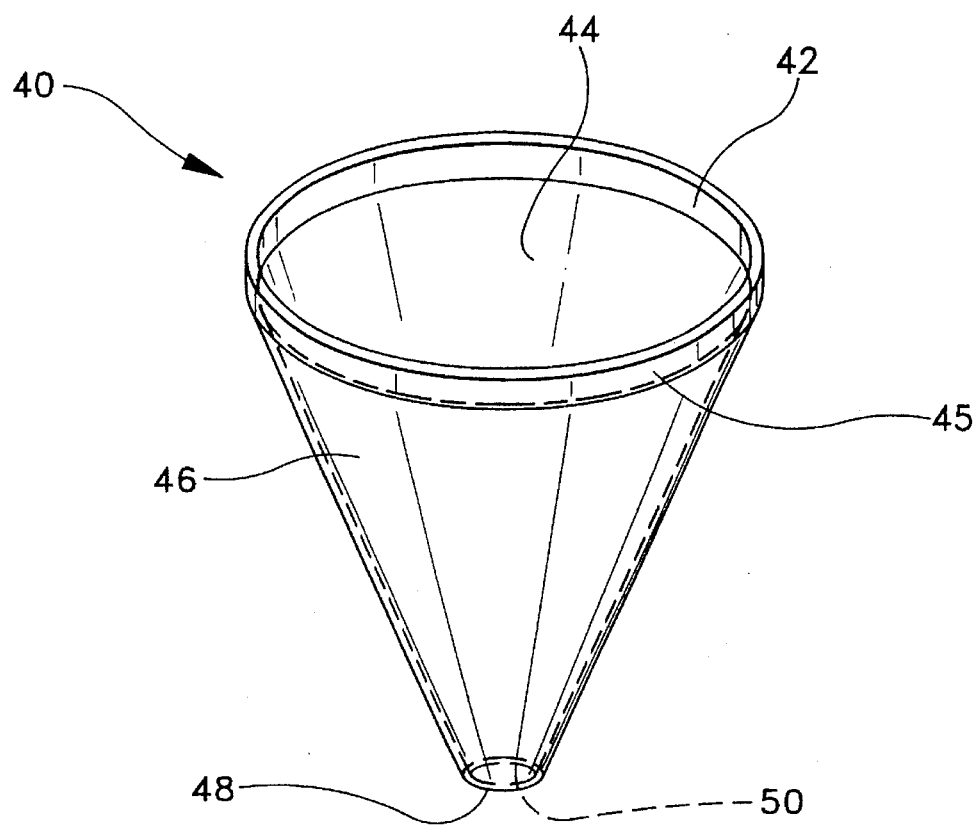

An insert 40 having the shape of a funnel is shown in FIG. 4, and includes a substantially annular top edge 42 defining an open end 44. A side wall has a substantially vertical section 45 and a tapered section 46 terminating at a substantially annular bottom edge 48 defining an open bottom end 50 which engages spike 24 during centrifugation.

The mechanical blood separating insert of the invention may be descendably immobilized in the tube by any suitable means. The insert and the tube may be sized to form an interference fit between inside wall surface 19 of tube side wall 18 and vertical side wall portions 36, 36a and 45 of the insert embodiments of FIGS. 2–4. Preferably, the interference fit is sufficiently tight to immobilize the insert in the upper portion of the tube, as shown in FIG. 1, until a blood sample in the tube has been separated into solid and liquid phases.

Preferably, the insert may be immobilized with a layer thixotropic gel. A preferred gel is formed from a polydimethylsiloxane-polyethyleneoxide (PDMS-PEO) copolymer surfactant containing about 0.1 to 1.5% by weight of a dibenzylidene sorbitol (DBS) gelling agent and optionally containing up to 50% by weight of water or alcohol. DBS gelling agents are disclosed in U.S. Pat. No. 5,186,972 of common assignee herewith and the surfactants are available from Union Carbide Corp. under the trade name SILWET™ surfactants. Preferred surfactants are SILWET™ L720, L722 and L7500. Preparation of the gels is described in Example I. Immobilization of the insert may be achieved with a layer of gel about 1 to 5 mm thick between the insert and inside wall of the tube. PDMS-PEO-DBS gels flow under the shear force of centrifugation to release the immobilized insert.

Figure 5:
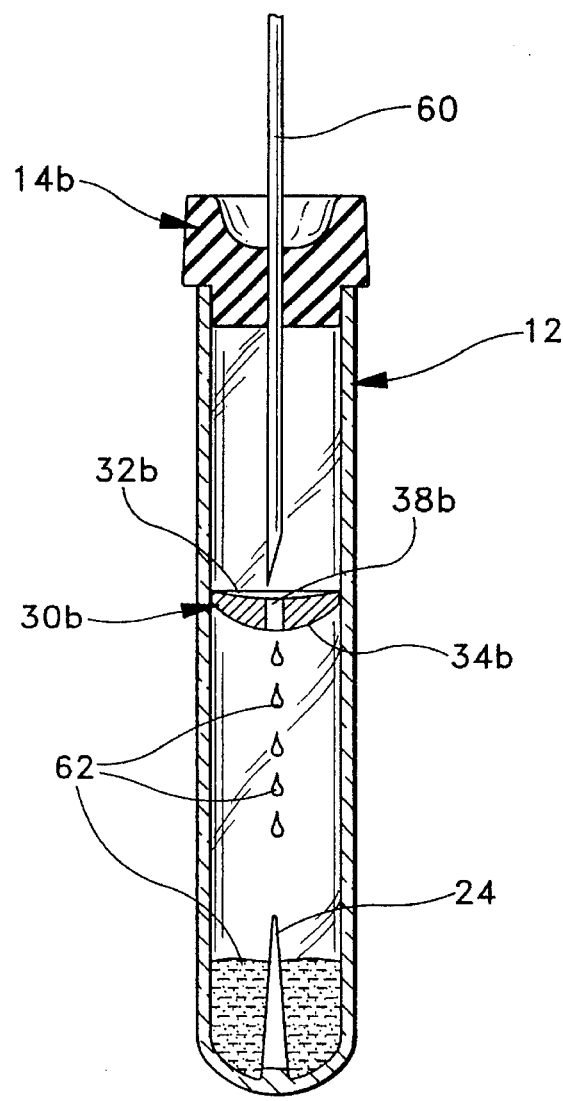
FIG. 5 illustrates the position of the insert during taking of a blood sample.
Figure 6:
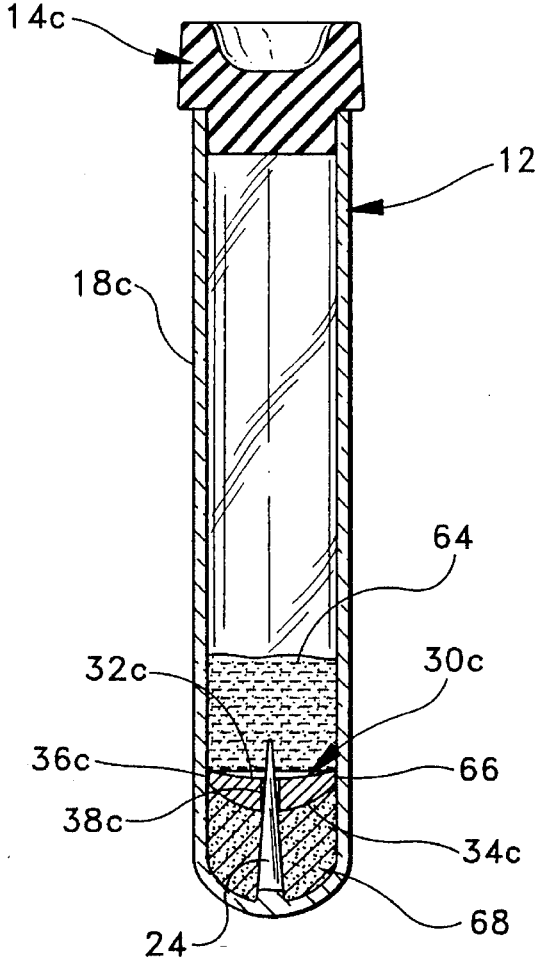
FIG. 6 shows the assembly of the invention after centrifugation of a blood sample.

FIGS. 5 and 6 illustrate use of the assembly during the collection of a blood sample and after centrifugation respectively. One end (not shown) of a double ended needle is inserted into a patient's vein and the other end 60 punctures stopper 14b. Blood is drawn from the needle into the tube by the pressure differential between the evacuated tube and the vein. The blood sample 62 may be delivered to the bottom of the tube through passageway 38b.

At this point, the sample may be centrifuged to give a liquid phase of plasma and a solid phase of packed cells. When the assembly is to be used to separate cells from plasma, an anticoagulant is preferably present in the tube. Any conventional anticoagulant, such as oxalate, EDTA, citrate or heparin may be used.

Alternatively the blood may be induced to clot so that on centrifugation the fluid phase is serum and the solid phase is a clot. Clotting may be induced by any suitable means, as described below, and preferably is substantially complete prior to centrifugation.

Centrifugation may be carried out conventionally starting from rest and rising to 1000 to 5000, preferably about 2200 G's of radial centrifugal force (rcf) wherein G is the force of gravity and 1 G is 9.8 m/sec$^2$ so that the solid phase separates from the liquid phase and packs in the bottom of the tube. As the centrifuge speeds up, the shear force of the centrifugation causes the gel to flow releasing the immobilized insert. The insert slowly descends whereby the separated liquid phase 64 flows through the passageway into the portion of the tube above the insert and the insert engages and seats on the spike. In the preferred embodiment of the invention, the insert mates with the spike at the interface 66 between liquid phase 64 and solid phase 68 and effectively separates the liquid above the insert from the solid below the insert.

The position in the tube at which the descending insert comes to rest on the spike is determined by the diameter of the passageway and the diameter of the spike. In order to determine the dimensions of the passageway and spike which will position the insert at the interface between the blood and solid phases, average values for the hematocrit may be used.

Hematocrit is the ratio of the volume occupied by the cellular components of a centrifuged blood sample to the total volume. For men, hematocrit averages 0.46, for women, 0.40. Thus a conventional blood sample draw of 6 ml will contain, after conventional centrifugation, about 2.4 to 2.76 ml of packed cells. Accordingly, the invention contemplates any combination of diameters of the passageway and spike at the point of contact which provide a volume within this range below the contact point for the packed cells. Most preferably, a contact point is selected which allows, for a 6 ml draw, about 2.8 to 3.0 ml for the packed cells, because a small quantity of serum or plasma below the insert is preferred to the presence of cells above the insert which have been forced upwardly through the passageway by a contact point which does not leave sufficient volume for the cells.

A conventional evacuated blood collection tube designed for a 6 ml blood draw is 100 mm in length and 13 mm in diameter. For such a tube, the contact point which leaves 2.8 ml below the insert is about 25 mm above the bottom of the tube. It is however apparent that the position of the contact point, and thus the diameters of the passageway and spike will depend on factors such as tube dimensions and volume of sample. It is further apparent that various combinations of passageway and spike diameters will provide a contact point at the proper height above the bottom of the tube. It is accordingly not intended to limit the invention to any particular combination of blood draw, tube size, passageway and spike diameters, and a determination of satisfactory dimensions for these elements is well within the purview of one skilled in the art.

In an alternative embodiment of the invention, the tube may be molded to have an annular projection extending from the inside wall surface of the tube into the interior volume upon which the descending insert may come to rest. The projection may be located at the position which leaves a volume below the immobilized insert for the packed cells, as described above.

The tube and spike may be of glass or preferably plastic. Suitable plastics are polypropylene (P), polyethylene terephthalate (PET) and polystyrene (PS). While the tube may be of any size, the invention is particularly well suited to evacuated blood collection tubes. These tubes are generally cylindrical, 50 to 150 mm in length and about 10 to 20 mm in diameter. The stopper may be of any elastomer, as is well known in the art of evacuated blood collection tubes. Likewise the insert may be of plastic, preferably PET or most preferably PS, and generally is manufactured by injection molding.

For the embodiment of the invention in which the blood sample is to be separated into serum and clot, it is preferred but not essential that the assembly of the invention includes a clot-activating feature. Any additive, structure or method for activating the clotting mechanism as known in the art may be used. Typical activators which may be present in the tube are diatomaceous earth, particles of inorganic silicates, or biochemicals such as ellagic acid and thromboplastin. The activator may be placed in the bottom of the tube or may be affixed to the wall of the tube.

Preferably, clot activation is accomplished by treating a surface which contacts the blood sample with a plasma generated from a suitable process gas. Thus, all or part of the inside wall of the tube or spike may be modified with a plasma to be clot-activating. A representative but not limiting list of suitable process gases includes nitrogen, ammonia, carbon dioxide, sulfur dioxide, air and oxygen wherein air and oxygen are preferred. The surface to be treated may be placed between the electrodes of a conventional plasma generator equipped with a pressure gauge, a gas inbleed and a vacuum connection. Suitable electrodes may be of any conducting material, although stainless steel and aluminum are preferred. The width and shape of the electrodes is not critical. Any suitable ionizing plasma may be used, as, for example, a plasma generated by a corona discharge or preferably a glow discharge.

A wide range of power settings, radio frequencies and duration of exposure of the plastic surface to the plasma may be used. Ranges for these parameters which provide advantageous results are DC or AC power levels up to 200 watts, from about 0.1 to about 50 megahertz and from about 0.1 to 30 minutes. preferred ranges are 10–50 watts, 10–20 megahertz and 2–10 minutes respectively. Any gas pressure may be used, however, gas pressures are advantageously maintained at 5 mm of Hg or below in order to benefit from reduced voltage requirements. Ambient temperature for plasma generation is preferred. Further details are not needed by one skilled in the art for a full understanding of this aspect of the invention.

The plasma treatment results in introduction of polar functional groups into the surface of the plastic. The functional group depends on the process gas used to generate the plasma. For example, after plasma treatment, the surface may contain oxygen, nitrogen or sulfur atoms. These groups cause the plasma-treated surface to have a clot activating property similar to and even somewhat greater than that of glass.

The assembly may contain, depending on the projected end use, any of a variety of additives known to be useful in blood separation or analysis.

EXAMPLE I

Preparation of Gel

A mixture of water soluble PDMS-PEO surfactant, (SILWET™ L-720), specific gravity 1.04, DBS (0.25,0.50,0.75 and 1.0 weight percent) and water (0,10,25 and 50 weight percent) in a glass test tube was heated in a sand bath at 175°–200° C. for about ½ hr. On cooling for about 1 to 48 hrs, the mixtures gelled. The gels did not flow.

In similar fashion, alcohol soluble surfactants SILWET™ L-722 and L-7500 were converted into gels with DBS either neat or with up to 50% isopropanol.

EXAMPLE II

Immobilization and Release of Insert in Tube

A glass insert in accordance with FIG. 4 was made by cutting off the end of a glass pipette so that the outside diameter of the top of the funnel was slightly smaller than the inside diameter of a 13×100 mm glass tube. The gel of Example I was heated until liquid and applied to the outer rim of the glass insert. The insert coated with gel was assembled into the glass tube 23 mm from the top of the tube. The assembly was cooled to room temperature and the gel reformed and served as a cement to hold the insert against the inside wall of the tube.

Whole citrated porcine blood was added to the tube and recalcified by addition of 200 uL of 0.2M $CaCl_2$. Blood was allowed to clot for 15 minutes while the tube was continuously rotated on a standard inverting hematology mixer after which the tube was centrifuged for 10 minutes in a fixed rotor hematology centrifuge. Upon inspection it was found that the funnel had released and descended to the cell- serum interface. The gel was found at the bottom of the tube.

EXAMPLE III

A 6 ml blood sample was taken in an evacuated assembly of the invention which includes a 13×100 mm PS tube treated with an oxygen plasma and the insert of FIG. 2 immobilized with the gel of Example I. The passageway and spike diameters were such that the insert seated on the spike at a point about 25 mm above the bottom of the tube, and the plasma was generated using a conventional planer diode system at about 50 mtorr and 50 watts of 13.56 $MH_2$ radio frequency power.

The tube was set aside for a sufficient time to allow the sample to clot, then centrifuged at 0 to 1100 rcf. The insert descended until seating on the spike. A clear serum layer was present above the insert and was cleanly decanted from a clot of packed cells below the insert.

What is claimed is:

1. A blood collection assembly comprising: p1 a) a container having a bottom wall and a side wall unitary therewith, said side wall defining an open end,a and puncturable stopper in said open end, said bottom wall,side wall and stopper enclosing an interior volume; p1 b) mechanical means in said interior volume for separating liquid and solid blood phases, said means being immobilized to said side wall until released to descend during centrifugation; and p1 c) terminating means unitary with and projecting from a wall of said container for terminating descent of said mechanical means between said liquid and solid phases.

2. The assembly of claim 1 wherein said mechanical means is descendably affixed to said side wall by an interference fit.

3. The assembly of claim 1 wherein said mechanical means is descendably affixed to said side wall by a gel.

4. The assembly of claim 1 further comprising means for activating clotting of blood in said container.

5. A blood collection assembly comprising: p1 a) a tube having a bottom wall and a side wall unitary therewith, said side wall defining an open end, and a puncturable stopper in said open end, said bottom wall, side wall and stopper enclosing an evacuated interior volume; p1 b) an insert having a passageway therethrough in said tube, said insert being immobilized to an inside wall surface of said side wall until released to descend during centrifugation; and p1 c) a tapered spike unitary with and projecting upwardly from said bottom wall and axially aligned to said passageway for engaging a wall of said passageway.

6. The assembly of claim 5 further comprising an anticoagulant in said tube.

7. The assembly of claim 5 further comprising means in said tube for activating the clotting of blood in said tube.

8. The assembly of claim 7 wherein said means is a plasma-treated surface.

9. A method for preparing a blood sample for analysis comprising:

a) directing a blood sample into the interior volume of the assembly of claim 5;

b) centrifuging said sample to give a liquid phase and a solid phase, said centrifuging causing said insert to descend and seat on said spike at an interface between said solid and liquid phases; and c) separating said liquid phase above said insert from said solid phase below said insert.

10. The method of claim 9 further comprising the step of clotting said sample prior to said centrifuging.

* * * * *